(12) United States Patent
Berg

(10) Patent No.: US 9,238,596 B2
(45) Date of Patent: Jan. 19, 2016

(54) PROCESS SIMPLIFICATION FOR PRECURSOR COMPOUND

(75) Inventor: Tom Christian Berg, Oslo (NO)

(73) Assignee: GE Healthcare Limited, Buckinghamshire (GB)

( * ) Notice: Subject to any disclaimer, the term of this patent is extended or adjusted under 35 U.S.C. 154(b) by 1 day.

(21) Appl. No.: 13/994,781

(22) PCT Filed: Dec. 19, 2011

(86) PCT No.: PCT/EP2011/073204
§ 371 (c)(1),
(2), (4) Date: Jun. 17, 2013

(87) PCT Pub. No.: WO2012/084794
PCT Pub. Date: Jun. 28, 2012

(65) Prior Publication Data
US 2013/0274507 A1    Oct. 17, 2013

Related U.S. Application Data

(60) Provisional application No. 61/424,693, filed on Dec. 20, 2010.

(30) Foreign Application Priority Data

Dec. 20, 2010  (GB) .................................. 1021523.4

(51) Int. Cl.
| | | |
|---|---|---|
| *C07C 227/20* | (2006.01) | |
| *C07C 269/06* | (2006.01) | |
| *C07C 303/28* | (2006.01) | |
| *C07C 227/18* | (2006.01) | |
| *C07B 59/00* | (2006.01) | |

(52) U.S. Cl.
CPC ............. *C07B 59/001* (2013.01); *C07C 227/18* (2013.01); *C07C 227/20* (2013.01); *C07C 269/06* (2013.01); *C07C 303/28* (2013.01); *C07B 2200/05* (2013.01); *C07C 2101/04* (2013.01)

(58) Field of Classification Search
None
See application file for complete search history.

(56) References Cited

U.S. PATENT DOCUMENTS

| 7,264,792 | B2 | 9/2007 | Gibson et al. |
| 7,897,811 | B2 | 3/2011 | Hayashi et al. |
| 8,758,724 | B2 | 6/2014 | Ito et al. |
| 2010/0016626 | A1 | 1/2010 | Toyama et al. |

FOREIGN PATENT DOCUMENTS

| EP | 1978015 | 10/2008 |
| EP | 2230229 | 9/2010 |

OTHER PUBLICATIONS

Klyza et al. Nuclear Medicine and Biology, 2008, 35, 255-260.*
Wang, Et.Al. Heteroathom Chemistry, VCH Publishers, Derfield Beack FL, vol. 13, No. 1 Jan. 1, 2002 pp. 77-83.
PCT/EP2011/073204 ISRWO Dated Feb. 24, 2012.
GB10212523.4 Search Report Dated Mar. 23, 2011.

* cited by examiner

*Primary Examiner* — Yevegeny Valenrod
(74) *Attorney, Agent, or Firm* — Parks Wood LLC

(57) ABSTRACT

The invention relates to a process for preparation of radiopharmaceutical precursors, and in particular protected amino acid derivatives which are used as precursors for production of radiolabelled amino acids for use in in vivo imaging procedures such as positron emission tomography (PET). Particularly, the invention relates to a process for preparation of a precursor useful in the preparation of the [$^{18}$F]-1-amino-3-fluorocyclobutanecarboxylic acid ([$^{18}$F] FACBC) PET tracer.

15 Claims, No Drawings

PROCESS SIMPLIFICATION FOR PRECURSOR COMPOUND

This application is a filing under 35 U.S.C. 371 of international application number PCT/EP2011/073204, filed Dec. 19, 2011, which claims priority to Great Britain application number 1021523.4 filed Dec. 20, 2011 and to U.S. application No. 61/424,693 filed Dec. 20, 2010, the entire disclosure of which is hereby incorporated by reference.

TECHNICAL FIELD OF THE INVENTION

The present invention relates to a method to obtain radiopharmaceutical precursors, and in particular to protected amino acid derivatives which are used as precursors for production of radiolabelled amino acids for use in in vivo imaging procedures such as positron emission tomography (PET). The invention further includes a method to obtain said radiolabelled amino acids.

DESCRIPTION OF RELATED ART

In recent years, a series of radioactive halogen-labelled amino acid compounds including [$^{18}$F]1-amino-3-fluorocyclobutanecarboxylic acid ([$^{18}$F]-FACBC) have been designed as novel radiopharmaceuticals. [$^8$F]-FACBC is considered to be effective as a diagnostic agent for highly proliferative tumours, because it has a property of being taken up specifically by amino acid transporters. EP1978015(A1) provides precursors for the [$^{18}$F]-FACBC compound and methods to obtain said precursors. EP1978015(A1) specifically discloses a method to obtain the precursor 1-(N-(t-butoxycarbonyl) amino)-3-[((trifluoromethyl)sulfonyl)oxy]-cyclobutane-1-carboxylic acid ethyl ester wherein said method comprises the following steps:

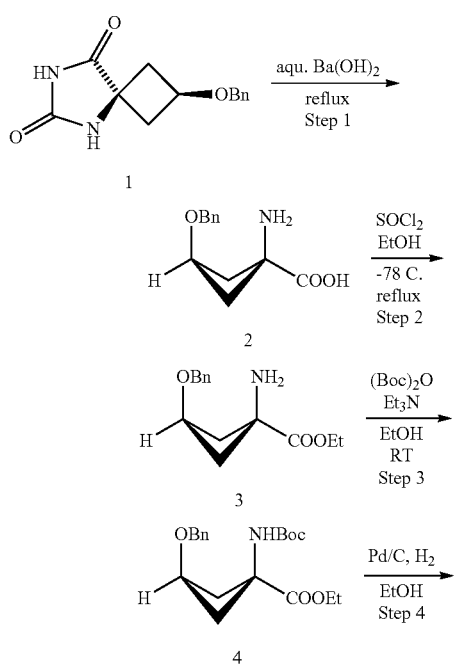

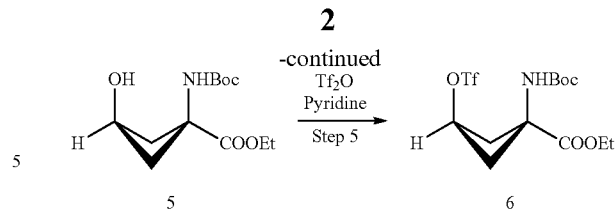

EP1978015(A1) describes that step 1 of the above reaction scheme comprises hydrolysis of syn-5-(3-benzyloxycyclobutane)hydantoin 1 by addition of barium hydroxide Ba(OH)$_2$ to the solution and refluxing the mixture at 114° C. for 24 hours or longer. In the ethyl esterification step 2, syn-1-amino-3-benzyloxycyclobutane-1-carboxylic acid 2 is dissolved in ethanol (EtOH) and reacted with thionyl chloride (SOCl$_2$) to yield syn-1-amino-3-benzyloxycyclobutane-1-carboxylic acid ethyl ester 3. Step 3 comprises addition of tert-butoxycarbonyl (Boc) to the amine function by reaction of 3 with tert-butyl dicarbonate (Boc)$_2$O, and the resultant material is purified by chromatography to obtain syn-1-(N-(t-butoxycarbonyl)amino)-3-benzyloxy-cyclobutane-1-carboxylic acid ethyl ester 4. The benzyl-protected intermediate 4 is then deprotected in step 4 by dissolving compound 4 in ethanol (EtOH), adding palladium on activated carbon (Pd/C) and applying a small positive H$_2$-pressure over the reaction mixture. The resultant material is purified by chromatography to yield syn-1-(N-(t-butoxycarbonyl)amino)-3-benzyloxy-cyclobutane-1-carboxylic acid ethyl ester 5 for use in step 5, which comprises reaction of 5 with trifluoromethanesulfonic anhydride (Tf$_2$O), followed by chromatographic purification with subsequent re-crystallization of the material in order to obtain syn-1-(N-(t-butoxycarbonyl)amino)-3-[((trifluoromethyl)sulfonyl)oxy]-cyclobutane-1-carboxylic acid ethyl ester 6. Similar methods are described in EP2230229 and US2010016626. In the case of all of these prior art teachings, the methods are suitable for small scale preparation for research purposes.

It would be desirable to reduce the complexity of the above-described multistep chemical reaction in order to reduce process time, use of equipment and chemicals, and to facilitate scale-up.

SUMMARY OF THE INVENTION

The present invention is a method for the preparation of precursor compounds for [$^{18}$F]-FACBC and similar compounds that is simplified with respect to known methods. The method of the invention leaves out one of the purification steps taught by the prior art and as such permits the resultant precursor compounds to be obtained in a more cost- and time-efficient manner.

DETAILED DESCRIPTION OF THE INVENTION

In one aspect, the present invention relates to a method to obtain a compound of Formula (I):

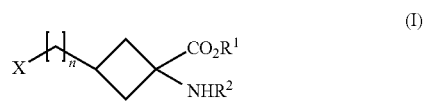

wherein:
R$^1$ represents a C$_{1-5}$ straight- or branched-chain alkyl group;

$R^2$ represents an amino protecting group;

X represents a leaving group selected from a halogen, or the group —O—$SO_2$—$R^3$ herein $R^3$ is a halogen, a straight-chain or branched-chain $C_{1-10}$ alkyl, a straight-chain or branched-chain $C_{1-10}$ haloalkyl, and a $C_{6-10}$ aryl; and, n is an integer of 0 to 4;

wherein said method comprises.

(a) debenzylation of a compound of Formula Ia:

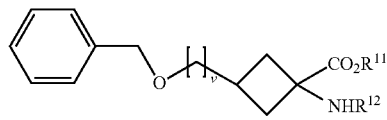
(Ia)

wherein $R^{11}$, $R^{12}$ and v are as defined for $R^1$, $R^2$ and n of Formula I, respectively;

to yield a compound of Formula Ib:

(Ib)

wherein $R^{21}$, $R^{22}$ and v are as defined for $R^1$, $R^2$ and n of Formula I, respectively;

(b) conversion of the compound of Formula Ib obtained directly from step (a) into a compound of Formula I by reaction with a suitable formula of X as defined above for Formula I.

The term "alkyl" used alone or in combination means a straight-chain or branched-chain group having the general formula $C_nH_{2n+1}$. The value of n in this general formula is specified in particular cases. Examples of some preferred alkyl groups include methyl, ethyl, 1-propyl or isopropyl groups.

By the term "protecting group" is meant a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Fourth Edition, John Wiley & Sons, 2007). Suitable amino protecting groups are well-known in the art. A suitable amino protecting group $R^2$ is a carbamate. Preferably $R^2$ is selected from; tert-butyl carbamate (BOC), 9-fluoroenylmethyl carbamate (Fmoc), methyl carbamate, ethyl carbamate, 2-chloro-3-indenylmethyl carbamate (Climoc), benz[f]inden-3-ylmethyl carbamate (Bimoc), 2,2,2-trichloroethyl carbamate (Troc), 2-chloroethyl carbamate, 1,1-dimethyl-2,2-dibromoethyl carbamate (DB-t-BOC), 1,1-dimethyl-2,2,2-trichloroethyl carbamate (TCBOC), benzyl carbamate (Cbz) and diphenylmethyl carbamate. Most preferably $R^2$ is tert-butyl carbamate, to provide a N-tert-butoxycarbonyl.

The term leaving group refers to a moiety suitable for nucleophilic substitution and is a molecular fragment that departs with a pair of electrons in heterolytic bond cleavage.

The term "halogen" or "halo-" used alone or in combination refers to a substituent selected from fluorine, chlorine, bromine or iodine.

The term "$C_{1-10}$ haloalkyl" refers to an alkyl group as defined above comprising between 1-10 carbon atoms wherein at least one hydrogen is replaced with a halogen, wherein halogen is as defined above.

The term "$C_{6-10}$ aryl" refers to a monovalent aromatic hydrocarbon having a single ring phenyl) or fused rings (i.e. naphthalene). Unless otherwise defined, such aryl groups typically contain from 6 to 10 carbon ring atoms.

The term "debenzylation" refers to the cleavage of a benzyl substituent from a compound. The term "benzyl" refers to a group with chemical structure $C_6H_5CH_2$—. Debenzylation is a method well-known in the art and is generally carried out by "catalytic hydrogenation", which is a reaction whereby a carbon-carbon bond is cleaved or undergoes "lysis" by hydrogen. Hydrogenolysis is usually carried out catalytically, e.g. using palladium on carbon (Pd/C) as a catalyst. When a catalyst such as Pd/C is used in the debenzylation step, the catalyst is removed from the reaction mixture by filtration prior to the next step. The term "filtration" refers to the mechanical separation of solids from fluids. Non-limiting examples of suitable filtration means for use in the present invention include glass sinter funnel or glass fibre filer in addition to a filter funnel, although other more specialised filter methods are also suitable. Generally, following the debenzylation step (a) and prior to the conversion step (b), the reaction solvent is removed by drying. Drying may be carried out by methods well-known to the person skilled in the art e.g. by evaporation under nitrogen flow and/or vacuum drying.

The term "obtained directly" refers to the fact that following step (a) and prior to step (b), no purification steps are carried out on the reaction mixture. In particular, the reaction mixture obtained by carrying out step (a) is not further purified by chromatography prior to carrying out step (b). Alternatively stated, step (a) is carried out with the proviso that the reaction mixture obtained from step (a) is not purified prior to carrying out step (b), and in particular with the proviso that the reaction mixture of step (a) is not purified by chromatography following step (a) and prior to step (b). The term "chromatography" is ell-known in the art and refers to a laboratory technique for the separation of chemical substances from each other in a mixture of different substances. Chromatographic separation involves passing the mixture dissolved in a mobile phase through a stationary phase, which separates the molecule of interest from other molecules in the mixture based on differential partitioning between the mobile and stationary phases.

The term "a suitable form of X" means X as defined herein in a form that can displace the hydroxyl function in a substitution reaction.

A compound of Formula Ia may be obtained by following or adapting the methods described in EP1978015(A1). For example, compound 4 as specifically described in EP1978015(A1) is a compound of Formula Ia suitable for use in the method of the present invention. The method described in EP1978015(A1) to obtain said compound 4 is illustrated in Scheme 1 below:

Scheme 1

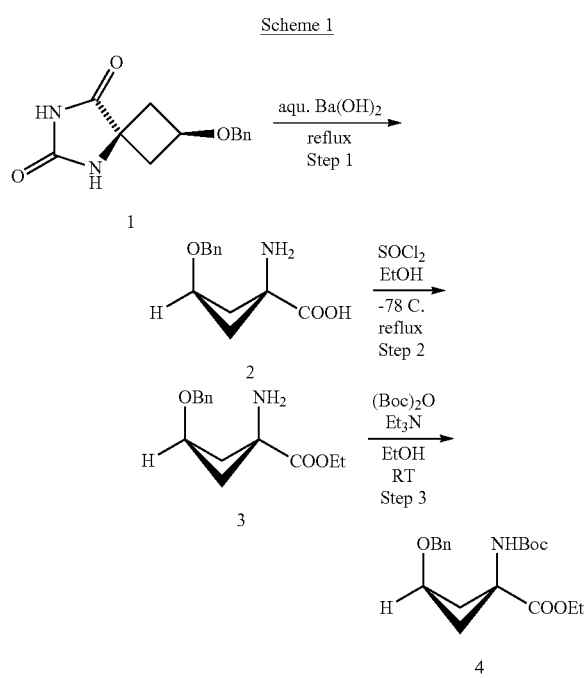

McConathy et al (Appl Rad Isotop 2003; 58: 657-666) also describe methods to obtain compounds of Formula Ia. In FIG. 2 of McConathy et al compound 6 is a compound of Formula Ia. The method described by McConathy et al to obtain said compound 6 is illustrated in Scheme 2 below:

Scheme 2

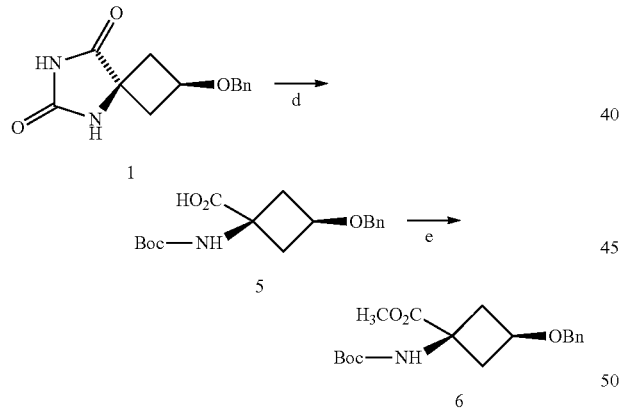

Hydantoin 1 was treated with 3N aqueous sodium hydroxide at 180° C. followed by di-tertbutyl dicarbonate to provide the N-Boc acid 5. Methyl ester 6 was obtained in high yield by reacting 5 with trimethylsilyl diazomethane.

It is within the ordinary skill in the art to adapt the above-described prior art methods to obtain other compounds of Formula Ia that fall within the definition of the present invention. Suitably, the starting hydantoin compound includes a mixture of the syn- and anti-enantiomers. There is no need for actively separating enantiomers, at any stage of the process.

In a preferred embodiment of the invention, X is the group —O—SO$_2$—R$^3$. Most preferably when X is O—SO$_2$—R$^3$ it is selected from the group consisting of toluenesulfonic acid, nitrobenzenesulfonic acid, benzenesulfonic acid, trifluoromethanesulfonic acid, fluorosulfonic acid, and perfluoroalkylsulfonic acid. In an especially preferred embodiment —O—SO$_2$—R$^3$ is trifluoromethanesulfonic acid. The group —O—SO$_2$—R$^3$ can be added in step (b) of the method of the invention by reaction of the compound of Formula Ib with an electrophilic derivative of the desired —O—SO$_2$—R$^3$ group, which is an example of a "suitable form of X" For example, where it is desired to add trifluoromethanesulfonic acid, the compound of Formula Ib can be reacted with trifluoromethanesulfonic anhydride.

In an alternative preferred embodiment, X is halogen. When X is halogen it is most preferably bromo or chloro. Step (b) of the method of the invention wherein X is a halogen may be carried out by methods well known to those skilled in the art. For example, compound of Formula I wherein X is chloro can be obtained by reaction of the compound of Formula Ib with a chloride-containing reagent such as thionyl chloride, phosphorous pentachloride (PCl$_5$), phosphorous trichloride (PCl$_3$), each of which are examples of a "suitable form of X". A compound of Formula I wherein X is bromo can be obtained by reaction of a compound of Formula Ib with a bromine-containing reagent such as hydrobromic acid (HBr) or phosphorous tribromide (PBr$_3$), again, each of which are examples of a "suitable foam of X".

Preferably, R$^1$ is methyl or ethyl and is most preferably ethyl. This preferred definition of R$^1$ equally applies to R$^{11}$ and R$^{21}$.

R$^2$ is preferably a carbonate ester protecting group wherein the term "carbonate ester" refers to a functional group consisting of a carbonyl group flanked by two alkoxy groups having general structure R$^x$O(C═O)OR$^y$. R$^1$ is most preferably a t-butoxycarbonyl group. This preferred definition of R$^2$ equally applies to R$^{12}$ and R$^{22}$.

Preferably, n is 0 or 1 and is most preferably 0. This preferred definition of n equally applies to v and w.

In a particularly preferred embodiment of the method of the present invention said compound of Formula I is:

Compound 1

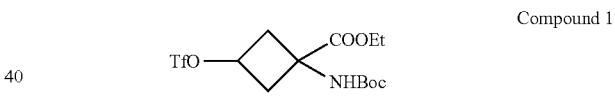

said compound of Formula Ia is:

Compound 1a

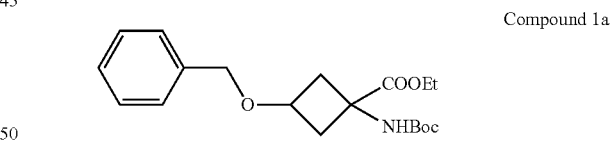

and said compound of Formula Ib is:

Compound 1b

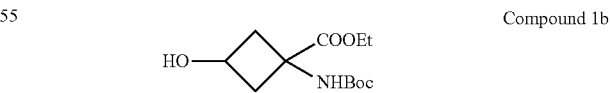

wherein Et is ethyl, OTf is triuoromethanesulfonic acid and Boc is tert-Butyloxycarbonyl.

The method of the present invention shortens process time and reduces cost of goods in comparison to the prior art methods as it is possible to perform two consecutive reaction steps without purification of the material obtained from the de-benzylation step. Introduction of this process change reduces the operation time due to removal of one chromatographic purification step. Conversion of the crude product comprising the compound of Formula Ib is done simply by re-dissolving the substance and then carrying out step (b) of the method. As demonstrated in the experimental examples below, in comparison to the prior art process the method of the invention results in a similar purity of the desired compound of Formula 1. A significant advantage of the method of the invention is that it is amenable to scale-up whereas the prior art methods are not. The process of the invention is therefore particularly useful when preparing in large scale, such as when preparing 100 grams or more, such as 300 grams, or up to 500 grams or more.

The compound of Formula I obtained by the method of the invention is a useful precursor compound in the radiosynthesis of certain $^{18}F$-labelled compounds. Therefore, the present invention also provides a method to obtain a compound of Formula II:

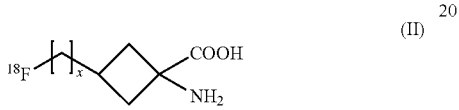
(II)

wherein x is as defined for n above;
and wherein said method comprises the method as defined herein to obtain the compound of Formula I and the further steps:
(c) reaction of the compound of Formula I as defined herein with a suitable source of $^{18}F$-fluoride to obtain a compound of Formula IIa.

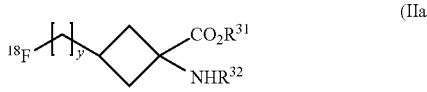
(IIa)

wherein $R^{31}$, $R^{32}$ and y are as defined herein for $R^1$, $R^2$ and n, respectively; and,
(d) deprotection of the compound of Formula IIa obtained in step (d) to remove $R^{31}$ and $R^{32}$.

Typically, [$^{18}F$]-fluoride ion is obtained as an aqueous solution which is a product of the irradiation of an [$^{18}O$]-water target. It is common to carry out various steps in order to convert [$^{18}F$]-fluoride into a reactive nucleophilic reagent, such that it is suitable for use in nucleophilic radiolabelling reactions. As with non-radioactive fluorinations, these steps include the elimination of water from [$^{18}F$]-fluoride ion and the provision of a suitable counterion (Handbook of Radiopharmaceuticals 2003 Welch & Redvanly eds. Chapter 6 pp 195-227). The radiofluorination reaction is then carried out using anhydrous solvents (Aigbirhio et at 1995 J Fluor Chem; 70: pp 279-87).

To improve the reactivity of [$^{18}F$]-fluoride ion for fluoridation reactions a cationic counterion is added prior to the removal of water. The counterion should possess sufficient solubility within the anhydrous reaction solvent to maintain the solubility of the [$^{18}F$]-fluoride ion. Therefore, counterions that have been used include large but soft metal ions such as rubidium or caesium, potassium complexed with a cryptand such as Kryptofix™, or tetraalkylammonium salts. A preferred counterion for fluoridation reactions is potassium complexed with a cryptand such as Kryptofix™ because of its good solubility in anhydrous solvents and enhanced fluoride reactivity.

Step (d) of deprotection is carried out by methods that are well-known to those of skill in the art. A wide range of protecting groups as well as methods for their removal are described in 'Protective Groups in Organic Synthesis', Theorodora W. Greene and Peter G. M. Wuts, (Fourth Edition, John Wiley & Sons, 2007). In a preferred embodiment, the carboxy protecting group $R^{31}$ is removed prior to the amino protecting group $R^{32}$. For example, where $R^{31}$ is Et it may be removed by basic hydrolysis and where $R^{32}$ is Boc it may be subsequently removed by acidic hydrolysis.

The range of suitable and preferred definitions of n as provided above equally apply to x and y of Formulae II and IIa.

The range of suitable and preferred definitions of $R^1$ and $R^2$ as provided above equally apply to $R^{31}$ and $R^{32}$, respectively of Formulae II and IIa.

In a preferred embodiment said compound of Formula II is:

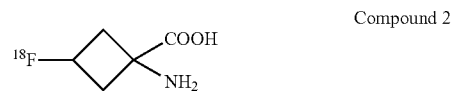
Compound 2 and said compound of Formula IIa is:

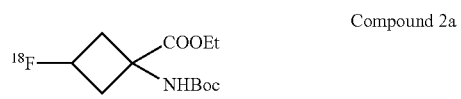
Compound 2a wherein Et is ethyl and Boc is tert-Butyloxycarbonyl.

In a preferred embodiment, steps (c) and (d) are carried out on an automated synthesiser. [$^{18}F$]-radiotracers are now often conveniently prepared on an automated radiosynthesis apparatus. There are several commercially-available examples of such apparatus, including Tracerlab™ and Fastlab™ (both from GE Healthcare Ltd). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

A typical cassette for automated synthesis of a compound of Formula II includes:
(i) a vessel containing a compound of Formula I as defined herein; and
(ii) means for eluting the vessel with a suitable source of [$^{18}F$]-fluoride as defined herein.
(iii) an ion-exchange cartridge for removal of excess [$^{18}F$]-fluoride; and,
(iv) a cartridge for deprotection of the compound of Formula IIa to form the compound of Formula II.

The invention will now be described by means of the following experimental examples:

BRIEF DESCRIPTION OF THE EXAMPLES

Example 1 describes the synthesis of 5-(3-benzyloxycyclobutane)hydantoin.
Example 2 describes the synthesis of 1-amino-3-(benzyloxy)cyclobutanecarboxylic acid.
Example 3 describes the synthesis of 1-Amino-3-benzyloxy-cyclobutanecarboxylic acid ethyl ester.
Example 4 describes the synthesis of Compound 1a.

Example 5 describes the synthesis of purified Compound 1b.

Example 6 describes the synthesis of Compound 1b without purification.

Example 7 describes the prior art synthesis of Compound 1 using purified Compound 1b.

Example 8 describes the inventive synthesis of Compound 1 using crude Compound 1b.

LIST OF ABBREVIATIONS USED IN THE EXAMPLES

DCM dichloromethane
EtOAc ethyl acetate
$Et_2O$ diethyl ether
$Et_3N$ triethylamine
g gram(s)
hr hour(s)
l liter(s)
min minute(s)
ml milliliter(s)
mol mole(s)
sat.aq saturated aqueous
TLC thin layer chromatography
w/w weight for weight

EXAMPLES

Example 1

Synthesis of 5-(3-benzyloxycyclobutane)hydantoin

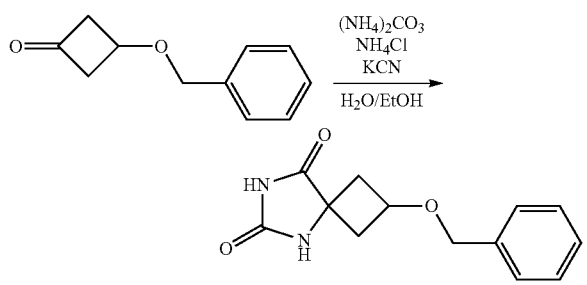

A reactor was charged with ammonium carbonate (1250 g, 13.0 mol) and ammonium chloride (279.9 g, 5.23 mol) and water (9.0 l). The resulting mixture was stirred at ambient temperature under $N_2$-atmosphere. 3-benzyloxycyclobutan-1-one (prepared according to the method described by McConathy et al Appl Radiat Isotop 2003; 58: 657-666) (230.0 g, 1.31 mol) dissolved in ethanol (8.51 l) was added slowly to the aqueous solution during 108 minutes, the resulting mixture was stirred for 70 minutes before KCN (383.8 g, 5.89 mol) was added. The resulting mixture was heated to 60° C. and stirred for 18 hours, cooled to ambient temperature and evaporated in vacuo at 53-56° C.

To the crude product was added water (1.7 l) to form a suspension which was gently stirred for 45 minutes. The suspension was filtered through a glass sinter funnel (pore size 3), the filter cake washed with cold water (1.2 l, 9.5° C.) and dried in vacuo at 27° C. for 16 hours 10 minutes.

Solid material from vacuum drying (257.2 g) was dissolved in water-isopropanol (15.0 l, 1:1). The solution was stirred at ambient temperature for 70 minutes and un-dissolved particles were removed by filtration through a glass sinter filter (pore size 3). Filtrate evaporated in vacuo at 45-49° C. to approximately ⅓ of the starting volume. The resulting slurry was cooled to 7.6° C., filtered through a glass sinter filter funnel (pore size 3) and washed with cold water (2.0 l, <7° C.). The filter cake was transferred to a Schott Duran glass bottle and in vacuo at 36° C. for 18 h 40 min. Yield: 229.6 g (71%).

$^1$H NMR (500 MHz, DMSO-$d_6$) δ (ppm): 10.63 (s, 1H, NH), 8.24 (s, 1H, NH), 7.38-7.27 (m, 5H, Bz) 4.32 (s, 1H, $CH_2$-Bz), 4.06-3.98 (m, 1H, CH-ring), 2.68-2.61 (m, 2H, $CH_2$-ring) and 2.24-2.16 (m, 2H, $CH_2$-ring).

Example 2

Synthesis of 1-amino-3-(benzyloxy)cyclobutanecarboxylic acid

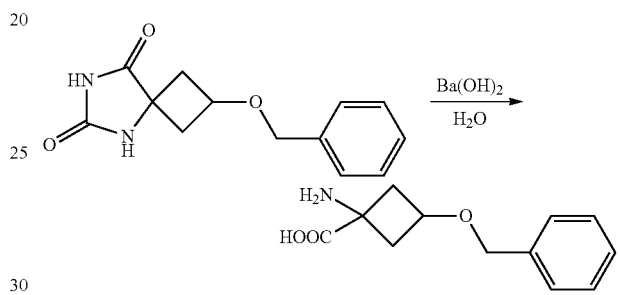

A reactor was charged with $Ba(OH)_2$ (450.5 g, 2.63 mol) and water (8.1 l). The resulting mixture was stirred at ambient temperature using a mechanical stirrer. 5-(3-benzyloxycyclobutane)hydantoin (229.6 g, 0.93 mol) was added to the reaction mixture and the remains of 5-(3-benzyloxycyclobutane)hydantoin from the bottle were washed with water (1.2 l) into the reactor. The resulting mixture was refluxed for 67 hours and 10 minutes (in-process HPLC samples were withdrawn to monitor the reaction progress).

The reaction mixture was cooled to ambient temperature, $H_2SO_4$ (110 ml, 1M) added and stirred for 8 min; the pH in the mixture was measured to pH 7. Precipitated barium salts were removed by filtration through a glass sinter funnel (pore size 3), the filter cake was washed with water (2.3 l) and filtrate evaporated vacuo at 55-60° C. 1-amino-3-(benzyloxy)cyclobutanecarboxylic acid was further dried in a vacuum oven at 50-60° C. for 20 h 54 min. Yield: 202.7 g (98.3%).

$^1$H NMR (500 MHz, $D_2O$) δ (ppm): 7.37-7.28 (m, 5H, Bz), 4.40 (s, 2H, $CH_2$), 4.30-4.23 (m, 1H, CH-ring), 2.79-2.71 (m, 2H, $CH_2$-ring) and 2.26-2.18 (m, 2H, $CH_2$-ring).

Example 3

Synthesis of 1-Amino-3-benzyloxy-cyclobutanecarboxylic acid ethyl ester

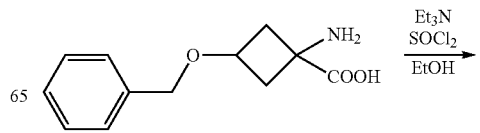

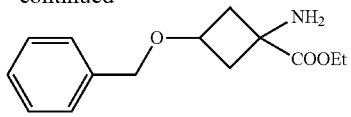

To a reactor charged with 1-amino-3-benzyloxy-cyclobutanecarboxylic acid (202.7 g, 0.94 mol) was added ethanol (7.0 l); the mixture was stirred at ambient temperature with mechanical stirring under an $N_2$-atmosphere for 18 minutes. To the reaction mixture was added $Et_3N$ (350 ml, 2.51 mol), cooled to −1.8° C. and $SOCl_2$ (170 ml, 2.4 mol) was added carefully keeping the reaction temperature <10° C. The reaction mixture was refluxed for 20 hours 10 minutes (reaction progress followed by TLC monitoring). Upon complete reaction the reaction mixture was cooled to 20° C. and evaporated in vacuo at 35° C. The weight of crude product including salts was 631.2 g.

$^1$H NMR (500 MHz, DMSO-$d_6$) δ (ppm): 7.38-7.27 (m, 5H, Bz), 4.41 (s, 2H, $CH_2$), 4.16 (q, 2H, $CH_2$), 4.07-4.01 (m, 1H, CH-ring), 2.77-2.70 (m, 2H, $CH_2$-ring), 2.26-2.19 (m, 2H, $CH_2$-ring) and 1.22 (t, 3H, $CH_3$).

Example 4

Synthesis of Compound 1a

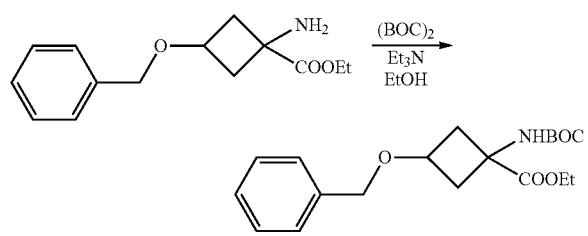

To a reactor charged with 1-amino-3-benzyloxy-cyclobutanecarboxylic acid ethyl ester (631.2 g, 2.53 mol) was added ethanol (18.5 l) and resulting mixture was stirred at ambient temperature with mechanical stirring under an $N_2$-atmosphere. $Et_3N$ (2.0 l, 14.3 mol) was added and the mixture was cooled to −8.5° C. before di-t-butyl di-carbonate (602.5 g, 2.76 mol) was added carefully. The resulting mixture was allowed to cool to ambient temperature and stirred for 20 hours (reaction progress followed by TLC monitoring). Upon complete reaction the mixture was evaporated in vacuo 35° C.

Crude product suspended in cold EtOAc (12.0 l, 3.8° C.) and transferred to a reactor with mechanical stirring and stirred for 15 min. Water (6.0 l) was added and the mixture stirred vigorously, phases separated and aqueous phase discarded. The organic phase was washed with cold HCl (12.0 l, 0.5M, 4.7° C.), water (6.0 l, 2×), $NaHCO_3$ (6.0 l, sat.aq), water (6.0 l) and NaCl (6.0 l, sat.aq., 2×) and dried over anhydrous $Na_2SO_4$ (2.52 kg, anhydrous) for 1 hour. The mixture was filtered through a glass sinter funnel (pore size 3), filter cake washed with EtOAc (2.6 l) and filtrate evaporated in vacuo at 38° C., crude=276 g. The crude product was re-dissolved in DCM (1000 ml) and adsorbed onto $SiO_2$ (611.5 g).

The crude product was purified by chromatographic purification using a Biotage Flash system with a 5 kg $SiO_2$ cartridge, gradient elution with 10-50% EtOAc in heptane. Product fractions combined and evaporated in vacuo at 33° C. to afford Compound 1a, yield: 233.7 g (73%).

$^1$H NMR (500 MHz, DMSO-$d_6$) δ (ppm): 7.73 (1H, NH), 7.38-7.26 (m, 5H, Bz), 4.37 (s, 2H; $CH_2$), 4.15-3.95 (m, 2H, $CH_2$ and m, 1H, CH-ring), 2.80-2.71 (m, 2H, $CH_2$-ring), 2.10-2.02 (m, 2H, $CH_2$-ring), 1.37 (s, 9H, $CH_3$, BOC), 1.22-1.11 (m, $CH_3$). Minor conformer not reported in NMR spectra.

Example 5

Synthesis and Purification of Compound 1b

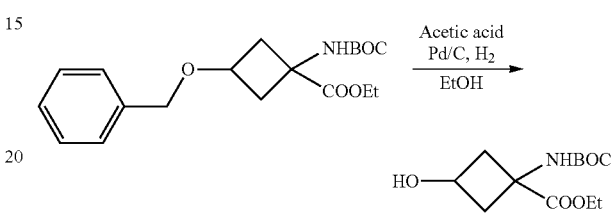

To a reaction flask charged with Compound 1a (31.83 g, 91 mmol) was added ethanol (600 ml) and acetic acid (8 ml, 139 mmol), an $N_2$-atmosphere was applied and the reaction flask was also connected to an $H_2$ supply. Moistened Pd on carbon (6.28 g, 10% w/w) was added to the mixture, and the reaction mixture was supplied with $H_2$-gas. The reaction mixture was stirred at ambient temperature for 2 days, until complete conversion (reaction progress monitored by TLC). The reaction mixture was filtered through a glass fibre filter, the filter cake washed with ethanol (160 ml) and the filtrate evaporated in vacuo at <40° C. to afford crude Compound 1b (24.64 g). The crude product re-dissolved in DCM (500 ml) and adsorbed onto $SiO_2$ (65 g).

The crude product was purified by flash chromatographic purification using $SiO_2$ (360 g) column, gradient elution with 30-70% EtOAc in heptane using heptane with 30% EtOAc as eluent. The product fractions were combined and evaporated in vacuo at 38° C. to afford Compound 1b 20.1 g (86%), purity GC 99.8%.

$^1$H NMR (500 MHz, DMSO-$d_6$) δ (ppm): 7.64 (1H, NH), 5.15 (1H, OH), 4.12-3.99 (m, 1H, CH-ring and m, 2H, $CH_2$), 2.75-2.66 (m, 2H, $CH_2$-ring), 2.02-1.93 (m, 2H, $CH_2$-ring), 1.37 (s, 9H, BOC) and 1.22-1.12 (m, 3H, $CH_3$).

Example 6

Synthesis of Compound 1b without Purification Prior to Use in Consecutive Reaction Step To a reaction flask charged with Compound 1a (8.5 g, 24.3 mmol) was added ethanol (155 ml) and acetic acid (2.13 ml, 37.2 mmol), an $N_2$-atmosphere was applied and the reaction flask was also connected to an $H_2$ supply. Moistened Pd on carbon (2.13 g, 10% w/w) was added the mixture, reaction mixture supplied with $H_2$-gas. The reaction mixture was stirred at ambient temperature for 2.25 days, until complete conversion (reaction progress monitored by TLC). The reaction mixture was filtered through a glass sinter filter, the filter cake washed with ethanol (40 ml) and the filtrate evaporated in vacuo <40° C. to afford crude Compound 1b (6.21 g). The substance was used in the consecutive reaction step without any further purification.

An NMR spectra not recorded in this reaction step.

Example 7

Synthesis of Compound 1 Using Purified Compound 1b (Prior Art Method)

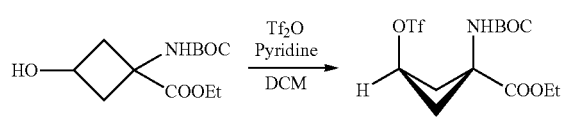

To a reaction flask charged with Compound 1b (20.1 g, 78 mmol) was added dichloromethane (500 ml) and pyridine (19 ml, 235 mmol), the resulting mixture was cooled to <5° C. Triflic anhydride (19.5 ml, 115 mmol) was added to the mixture in portions over 30 minutes, with the reaction temperature kept <5° C. during the addition. The resulting mixture was stirred on an ice-bath for 1 hour (reaction progress monitored by TLC) and upon complete reaction water (500 ml) was added to quench the reaction.

The reaction mixture was extracted with $Et_2O$ (950 ml), the water phase discarded, the organic phase washed with HCl (500 ml, 1M), brine (500 ml, sat.aq.) and dried over $Na_2SO_4$ (56 g). The mixture was filtered through a glass sinter filter, the filter cake washed with $Et_2O$ (100 ml) and the filtrate evaporated in vacuo <30° C. to afford crude Compound 1 (28.11 g). The crude product was re-dissolved in dichloromethane (400 ml) and adsorbed onto $SiO_2$ (80 g).

The crude product was purified by flash chromatographic purification using $SiO_2$ (330 g) column, isocratic elution with pentane:diethyl ether (3:1). The product fractions were combined and evaporated in vacuo at <30° C. to afford Compound 1 (21.9 g).

Compound 1 was further purified by re-crystallization by dissolving the material in diethyl ether (50 ml) and slowly stirring the mixture at <35° C. until all solids had dissolved. Reaction slowly cooled to 25° C. over 1 hour 5 minutes and further stirred at this temperature for 1 hour 20 minutes. The solution was further cooled to <5° C. and gently stirred for 20 minutes, the further cooled to <-20° C. for 15 minutes and stirred for 1 hour 30 minutes, ice cold heptane was added (110 ml) and the solution gently stirred for 1 hour 20 minutes. Formed crystals were collected by filtration using a pre-cooled glass sinter filter and washed with ice cold heptane (110 ml, <-5° C.). The reaction afforded Compound 1 19.47 g (64%), NMR purity +99%.

$^1$H NMR (500 MHz, DMSO-$d_6$) δ (ppm): 5.44-4.95 (m, 1H, CH-ring ands, br, 1H, NH), 4.26 (q, 2H, $CH_2$), 3.15-2.68 (m, 4H, 2×$CH_2$-ring), 1.45 (s, 9H, BOC) and 1.31 (t, 3H, $CH_3$)

Example 8

Synthesis of Compound 1 Using Crude Compound 1b (Method of the Present Invention)

The materials used in this reaction were not purified according to the prior art procedure. The only purification performed on the starting material Compound 1b was filtration through a glass sinter funnel followed by evaporation in vacuo to dryness.

Into a reaction flask charged with Compound 1b (3.0 g, 12 mmol) was added dichloromethane (77.5 ml) and pyridine (2.95 ml, 36.6 mmol), and the resulting solution cooled to <5° C. Triflic anhydride (3.01 ml, 17.9 mmol) was added to the mixture in portions over 23 minutes, with the reaction temperature kept at <5° C. during the addition. The resulting mixture was stirred on an ice bath for 31 minutes (reaction progress monitored by TLC) and upon complete reaction water (70 ml) was added to quench the reaction.

The reaction mixture was extracted with $Et_2O$ (150 ml), the water phase discarded, the organic phase washed with HCl (75 ml, 1M), brine (75 ml sat.aq.) and dried over $Na_2SO_4$. The mixture was filtered through a glass sinter filter and the filtrate evaporated in vacuo at <30° C. to afford crude Compound 1. The crude product was re-dissolved in dichloromethane (40 ml) and adsorbed onto $SiO_2$ (9.5 g).

The crude product was purified by flash chromatographic purification using $SiO_2$ column, isocratic elution with pentane:diethyl ether (3:1). The product fractions were combined and evaporated in vacuo at <30° C. to afford Compound 1 (3.22 g).

Compound 1 was further purified by re-crystallization by dissolving the material in diethyl ether (7.7 ml) and slowly stirring the mixture at <35° C. until all solids had dissolved. The reaction mixture was slowly cooled to 25° C. over 45 minutes and further stirred at this temperature for 1 hour 25 minutes. The solution was further cooled to <5° C. and gently stirred at this temperature for 54 minutes, then further cooled to <-20° C. and stirred at this temperature for 1 hour 4 minutes, ice-cold heptane (25 ml) was added and the solution gently stirred for 1 hour 20 minutes. Formed crystals were collected by filtration using a pre-cooled glass sinter filter and washed with ice cold heptane (25 ml, <-5° C.). The reaction afforded Compound 1 2.86 g (61%).

What is claimed is:

1. A method to obtain a compound of Formula (II):

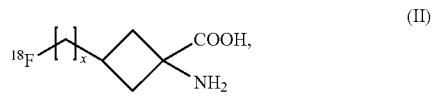

wherein x is an integer of 0 to 4; and wherein said method comprises:

(a) debenzylation of a compound of Formula Ia:

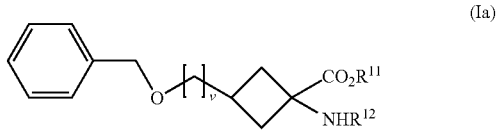

wherein:
  $R^{11}$ represents a $C_{1-5}$ straight- or branched-chain alkyl group;
  $R^{12}$ represents an amino protecting group; and,
  v is an integer of 0 to 4;
to yield a large scale batch of at least 100 g of a compound of Formula Ib:

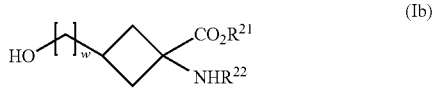

wherein $R^{21}$, $R^{22}$ and w are as defined for $R^{11}$, $R^{12}$ and v of Formula Ia, respectively and wherein said large scale batch is purified only by glass sinter filtration, followed by evaporation;

(b) conversion of the compound of Formula Ib obtained directly from step (a) into a compound of Formula I:

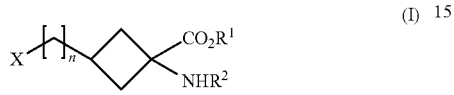

wherein $R^1$, $R^2$ and n are as defined for $R^{11}$, $R^{12}$ and v of Formula Ia, respectively; and, X represents a leaving group selected from a halogen, or the group —O—SO$_2$—R$^3$ wherein R$^3$ is a halogen, a straight-chain or branched-chain $C_{1-10}$ alkyl, a straight-chain or branched-chain $C_{1-10}$ haloalkyl, and a $C_{6-10}$ aryl;

wherein said conversion is carried out by reaction of said compound of Formula Ib with a suitable form of X as defined for Formula I;

(c) reaction of the compound of Formula I obtained in step (b) with a suitable source of $^{18}$F-fluoride to obtain a compound of Formula IIa:

wherein $R^{31}$, $R^{32}$ and y are as defined for $R^{11}$, $R^{12}$ and v of Formula Ia, respectively; and, (d) deprotection of the compound of Formula IIa obtained in step (c) to remove $R^{31}$ and $R^{32}$; and wherein said method provides a compound of Formula II suitable for use in in vivo imaging procedures.

2. The method as defined in claim 1 wherein X is a group represented by the group —O—SO$_2$—R$^3$.

3. The method as defined in claim 2 wherein R$^3$ is selected from the group consisting of toluenesulfonic acid, nitrobenzenesulfonic acid, benzenesulfonic acid, trifluoromethanesulfonic acid, fluorosulfonic acid, perfluoroalkylsulfonic acid, trimethylstannyl and triethylstannyl.

4. The method as defined in claim 3 wherein R$^3$ is trifluoromethanesulfonic acid.

5. The method as defined in claim 1 wherein X is halogen.

6. The method as defined in claim 5 wherein said halogen is bromo or chloro.

7. The method as defined in claim 1 wherein $R^1$ is ethyl.

8. The method as defined in claim 1 wherein $R^2$ is selected from the group consisting of a t-butoxycarbonyl group, an allyloxycarbonyl group, a phthalimide group and N-benzylideneamine substituent.

9. The method as defined in claim 1 wherein said compound of Formula I is:

said compound of Formula Ia is:

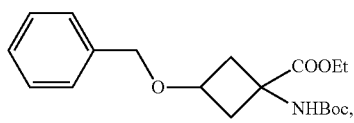 [SMILES: CCOC(=O)C1(NC(=O)OC(C)(C)C)CC(OCc2ccccc2)C1]

and said compound of Formula Ib is:

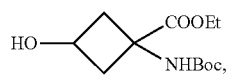

and wherein Et is ethyl, OTf is trifluoromethanesulfonic acid and Boc is tert-Butyloxycarbonyl.

10. The method as defined in claim 1 wherein said deprotection comprises removal of $R^{31}$ followed by removal of $R^{32}$.

11. The method as defined in claim 1 wherein $R^{31}$ is ethyl.

12. The method as defined in claim 1 wherein $R^{32}$ is a t-butoxycarbonyl group.

13. The method as defined in claim 1 wherein said compound of Formula II is:

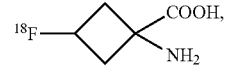

and said compound of Formula IIa is:

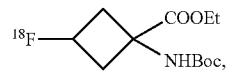

and wherein Et is ethyl and Boc is tert-Butyloxycarbonyl.

14. The method as defined in claim 13 wherein said deprotection step comprises removal of Et by basic hydrolysis and removal of Boc by acidic hydrolysis.

15. The method as defined in claim 1 wherein steps (c) and (d) are carried out on an automated synthesiser.

* * * * *